United States Patent [19]
Guardiani

[11] Patent Number: 5,033,286
[45] Date of Patent: Jul. 23, 1991

[54] ON-LINE INSTRUMENT FOR MEASURING EFFECTIVE PARTIAL PRESSURE OF DISSOLVED GASES IN A LIQUID

[75] Inventor: Richard F. Guardiani, Ohio Township, Allegheny County, Pa.

[73] Assignee: Westinghouse Electric Corp., Pittsburgh, Pa.

[21] Appl. No.: 539,948

[22] Filed: Jun. 18, 1990

[51] Int. Cl.⁵ .............................................. G01N 7/14
[52] U.S. Cl. ..................................... 73/19.1; 73/29.04
[58] Field of Search ................ 73/19.1, 19.05, 24.04, 73/64.2, 53, 29.01, 29.03, 29.04

[56] References Cited

U.S. PATENT DOCUMENTS

| 3,618,363 | 11/1971 | Kraus | 73/1 A |
| 4,366,700 | 1/1983 | Bouck | 73/19 |
| 4,373,374 | 2/1983 | Bajard | 73/19 |
| 4,394,635 | 7/1983 | Foss | 336/55 |
| 4,463,593 | 8/1984 | Parker | 73/19 |
| 4,702,102 | 10/1987 | Hammerton | 73/19 |

FOREIGN PATENT DOCUMENTS

| 570413 | 8/1977 | U.S.S.R. | 73/24.04 |
| 1415171 | 8/1988 | U.S.S.R. | 73/19.1 |
| 1441262 | 11/1988 | U.S.S.R. | 73/19.1 |

Primary Examiner—Hezron E. Williams
Assistant Examiner—Joseph W. Roskos

[57] ABSTRACT

An instrument for measuring on-line the effective partial pressure of dissolved gases in a liquid includes a housing having a flow chamber for connecting in flow communication with a flowing stream of liquid to be measured, and a streamlined V-shaped wing rotatably mounted to the housing and extending across the flow chamber for presenting different angles of attack to the stream of liquid flowing through the housing chamber. The wing has an apex which remains located at a center of the stream of liquid flowing through the housing chamber as the angle-of-attack of the wing is changed relative to the stream of liquid. An actuating mechanism is coupled to the wing for rotating and thereby changing the angle of attack of the wing relative to the stream of liquid flow. A device, such as a viewing window or an acoustical detector, is coupled to the housing for use in identifying the occurrence of incipient cavitation bubbles at the apex of the wing.

22 Claims, 6 Drawing Sheets

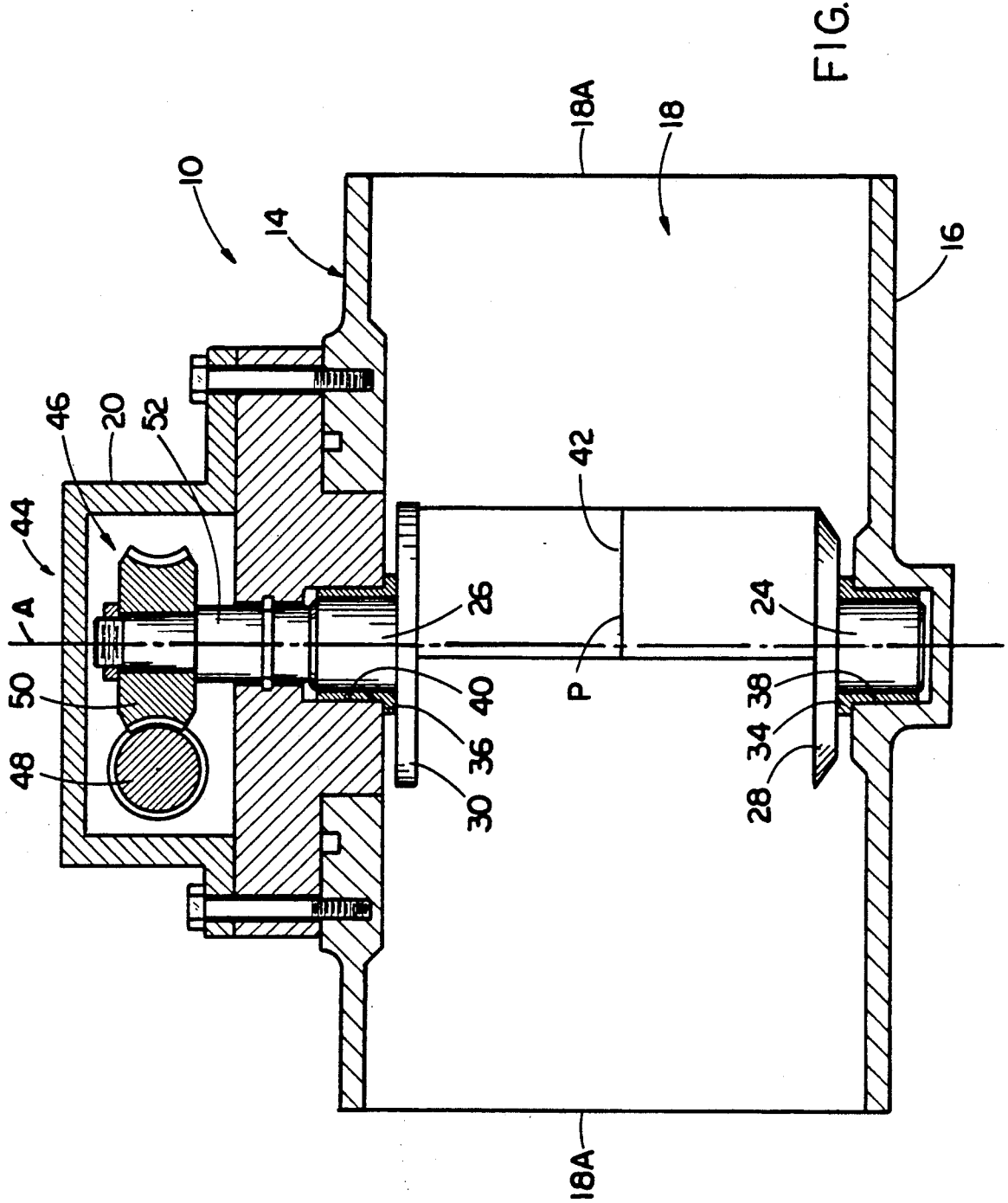

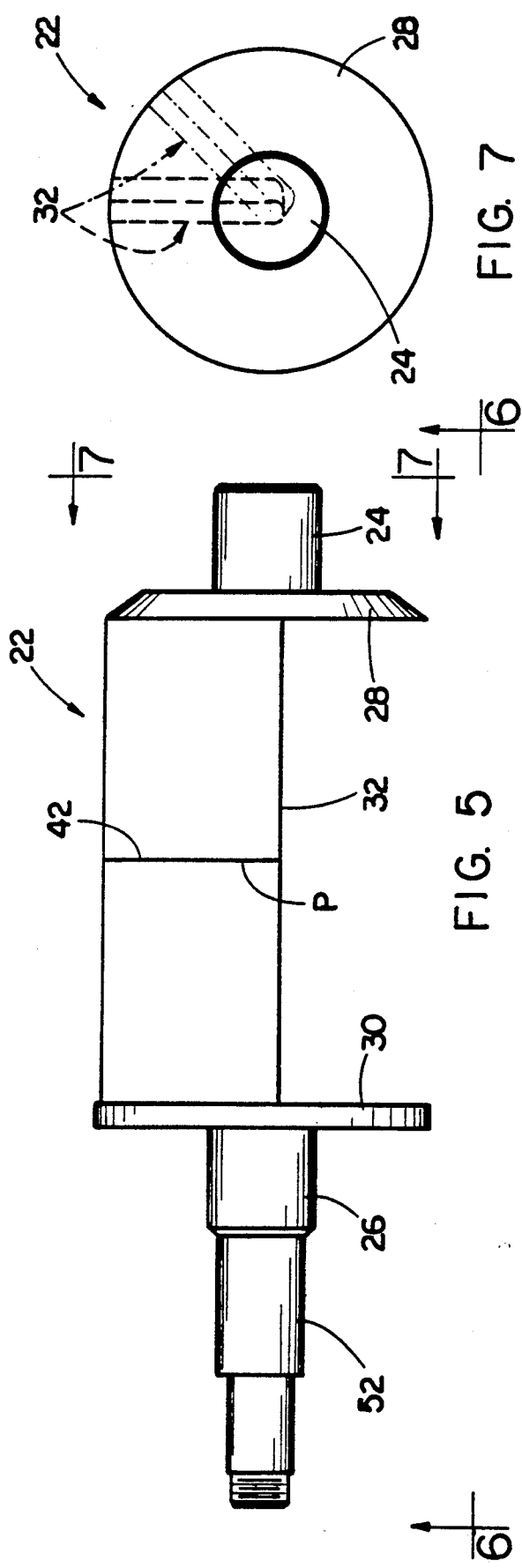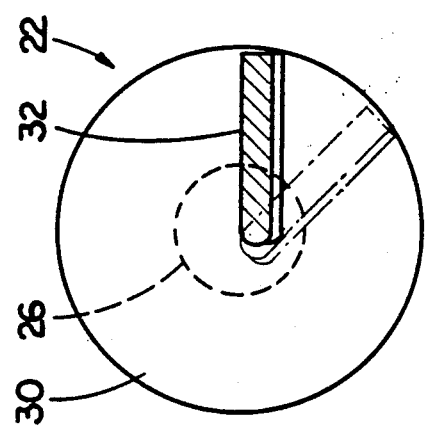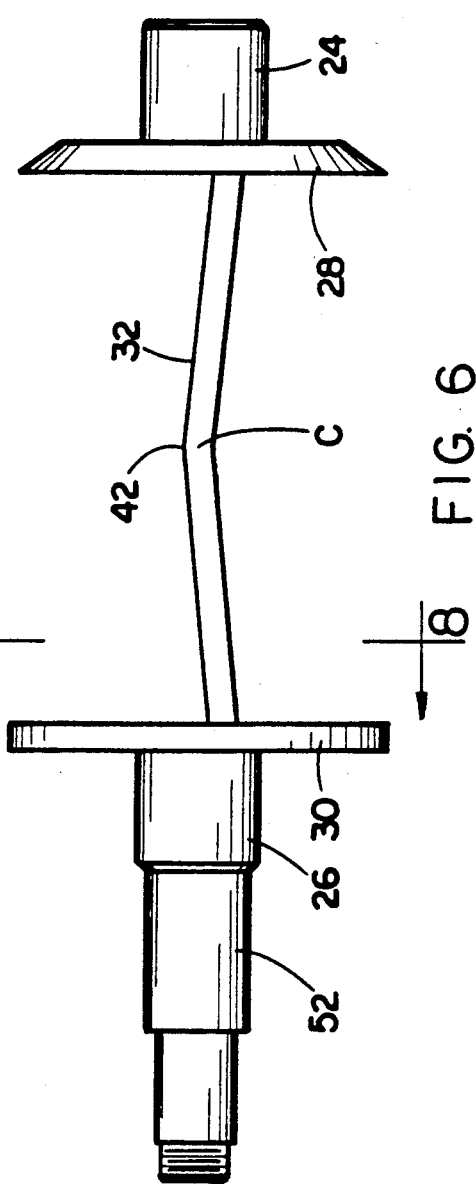

ON-LINE INSTRUMENT FOR MEASURING EFFECTIVE PARTIAL PRESSURE OF DISSOLVED GASES IN A LIQUID

BACKGROUND OF THE INVENTION

1. Field of the Invention

The present invention relates generally to measurement of the partial pressure of dissolved gases in a liquid and, more particularly, is concerned with an instrument for measuring on-line the effective partial pressure of dissolved gases in a liquid.

2. Description of the Prior Art

It is important in many fields to be able to know accurately and quickly the total effective partial pressure of dissolved gases in a liquid media. One field in which this is the case is the design and manufacture of centrifugal pumps.

Centrifugal pumps have a characteristic called required Net Positive Suction Head (NPSHr) NPSHr is a function of the hydraulic design of the pump and represents the minimum required margin between pump suction pressure and the vapor pressure of the pumped liquid. Failure to provide sufficient NPSHr may unduly restrict operation of the system in which the pump is installed. This is particularly true of nuclear reactor systems which have temperature/pressure restrictions due to brittle fracture concerns. Therefore, it is important for pump manufacturers to provide accurate NPSHr data for their pumps.

Pump manufacturers determine NPSHr by testing the pump. In the test procedure, the pump flow is held constant and the static suction pressure is decreased until one of the following events occurs: either cavitation bubbles appear on the impeller vanes (performed only if a viewport is available to look directly at the impeller suction eye), or the pump developed head falls off a certain amount (normally zero percent, one percent, or three percent head fall-off is used as the criteria). Then, the following formula is applied to determine NPSHr:

$$NPSHr = Ps + Pq - Pv,$$

where $P_s$ = the static suction pressure measured during the test.

$P_q$ = the velocity head pressure at the impeller suction which is obtained using the flow measured during the test and the suction diameter of the impeller which is known prior to test.

$P_v$ = the vapor pressure of the liquid being pumped.

The vapor pressure of the pumped liquid consists of the vapor pressure of the pure liquid (which is a function of temperature at the pump suction which is measured during testing) plus the effective vapor pressure of any dissolved gases.

The vapor pressure of the dissolved gases is normally determined using one of the following two prior art methods. A first method is to degas the test loop and assume that the partial pressure of the gases is zero or some fixed value. A second method is to obtain a sample of the pumped liquid in a bomb and analyze the sample for types of gases and content of each gas. Then, apply known laws of physics to determine partial pressure of the gases in the operating liquid.

The above prior art methods have significant disadvantages. The first method fails to achieve the desired degree of accuracy. The second method is unable to determine the gas pressure on-line. In addition, the second method also may not be as accurate as desired because while vaporization (cavitation) of a liquid is a thermodynamic process involving a change of phase, dissolved gases coming out of solution is a mass transport process which requires a considerable longer time span than the change of phase.

Consequently, a need exists for a way to accurately determine on-line the effective partial pressure of any dissolved gases in a liquid.

SUMMARY OF THE INVENTION

The present invention relates to an on-line measuring instrument designed to satisfy the aforementioned needs. The on-line measuring instrument of the present invention can accurately determine the effective partial pressure of any dissolved gases in a liquid without requiring any knowledge of the types of gases in liquid solution. Although, the instrument is particularly useful in the testing of centrifugal pumps for evaluating NPSHr, it may also be used in other applications where gas content or effective partial pressure of dissolved gases are required.

Accordingly, the present invention is directed to an instrument for measuring on-line the effective partial pressure of dissolved gases in a liquid. The on-line measuring instrument comprises: (a) a housing having a flow chamber for connecting in flow communication with a flowing stream of liquid to be tested; (b) a streamlined member, preferably in the form of a V-shaped wing, rotatably mounted to the housing and extending across the flow chamber for presenting different angles of attack to the stream of liquid flowing through the housing chamber, the member having a point, preferably constituted by an apex of the V-shaped wing, which remains located at a center of the stream of liquid flowing through the housing chamber as the angle-of-attack of the wing is changed relative to the stream of liquid flow; (c) means coupled to the wing for rotating and thereby changing the angle of attack of the wing relative to the flowing stream of liquid; and (d) means coupled to the housing for identifying the occurrence of incipient cavitation bubbles at the apex of the wing.

More particularly, the means for rotating the wing includes a drive train rotatably mounted to the housing and drivingly coupled to the wing. In an exemplary form, the drive train is a worm shaft and gear arrangement and includes a knob connected on the worm shaft for manually gripping and being rotatably mounted to housing.

The means for identifying the bubbles can take any one of several forms. In one form, it is a transparent viewing window mounted in the housing. In another form, it is a light source and detector arrangement for identifying the bubbles by detecting the scattering of light beam by the occurrence of the bubbles. In still another form, it is a detector for identifying the bubbles by detecting acoustic energy emitted upon collapse of the bubbles.

These and other features and advantages of the present invention will become apparent to those skilled in the art upon a reading of the following detailed description when taken in conjunction with the drawings wherein there is shown and described illustrative embodiments of the invention.

BRIEF DESCRIPTION OF THE DRAWINGS

In the course of the following detailed description, reference will be made to the attached drawings in which:

FIG. 4 is an axial sectional view of the instrument taken along line 4—4 of FIG. 2.

FIG. 5 is an enlarged side elevational view of a rotatable wing member of the instrument of FIG. 4 being removed from the instrument.

FIG. 6 is another side elevational view of the instrument wing member as seen along line 6—6 of FIG. 5.

FIG. 7 is an end elevational view of the instrument wing member as seen along line 7—7 of FIG. 5.

FIG. 8 is a transverse sectional view of the instrument wing member taken along line 8—8 of FIG. 6.

DETAILED DESCRIPTION OF THE INVENTION

Figure 1:
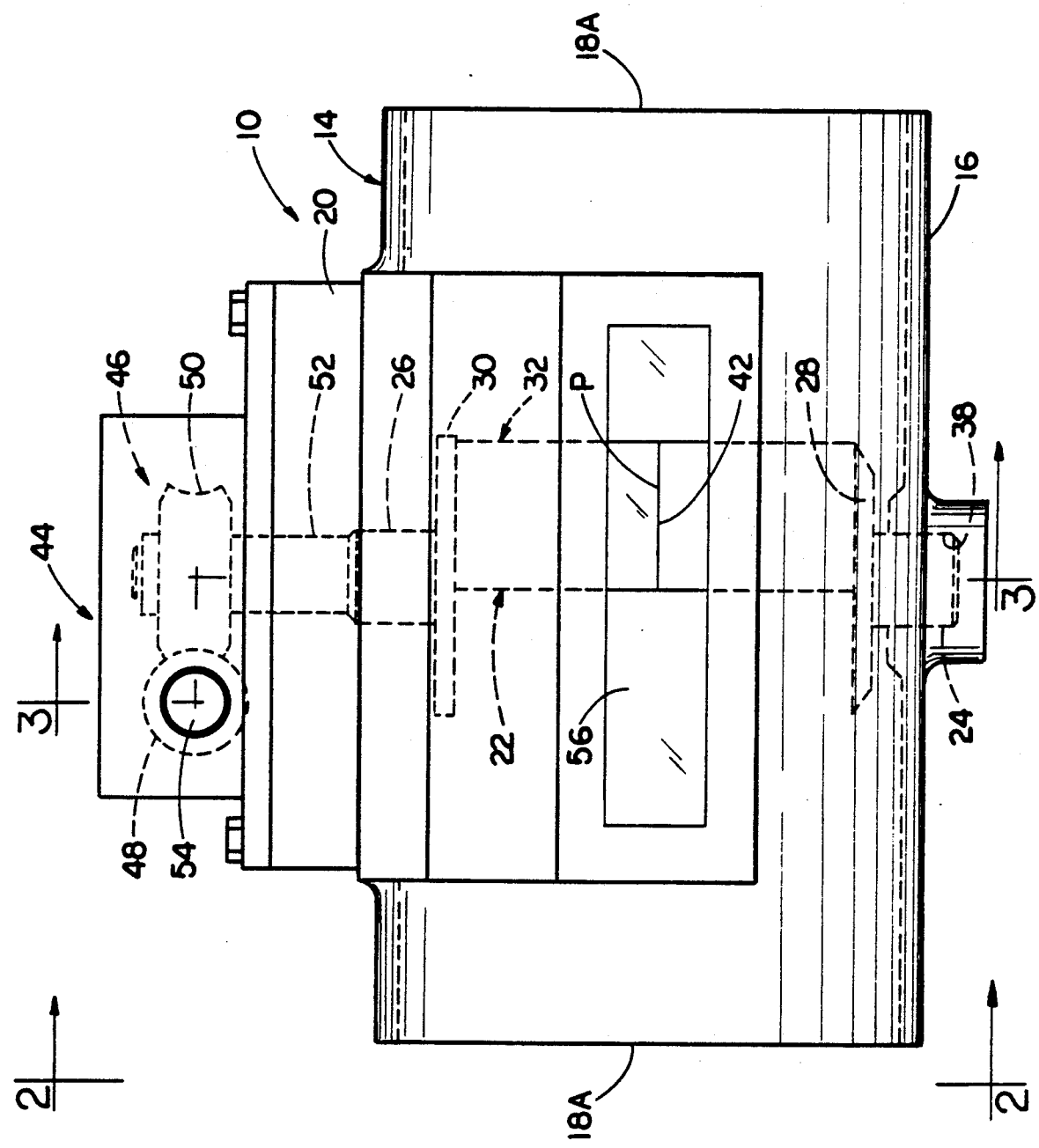
FIG. 1 is a side elevational view of an instrument for measuring on-line the effective partial pressure of dissolved gases in a liquid in accordance with the present invention.
Figure 2:
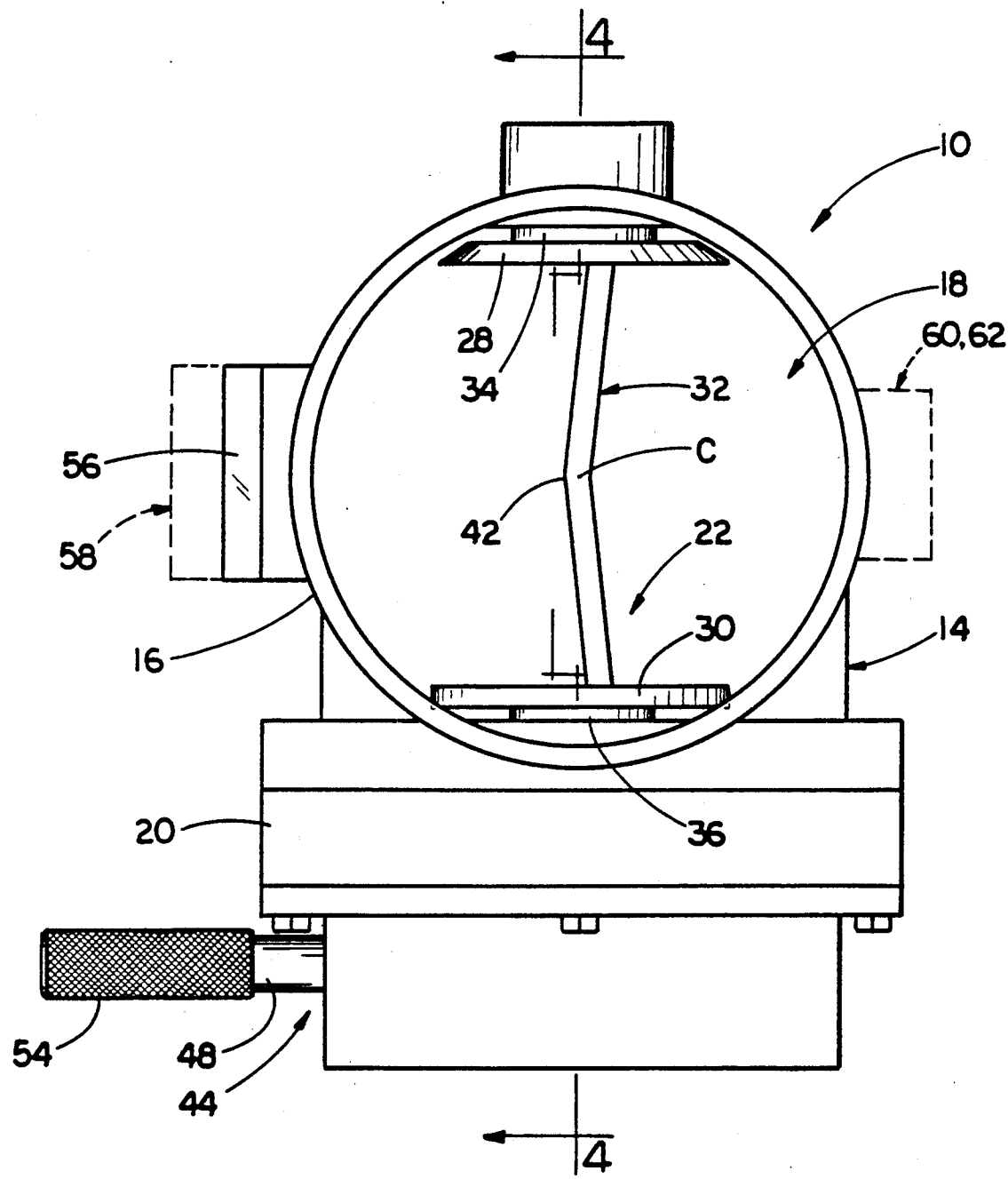
FIG. 2 is an end elevational view of the instrument as seen along line 2—2 of FIG. 1.
Figure 3:
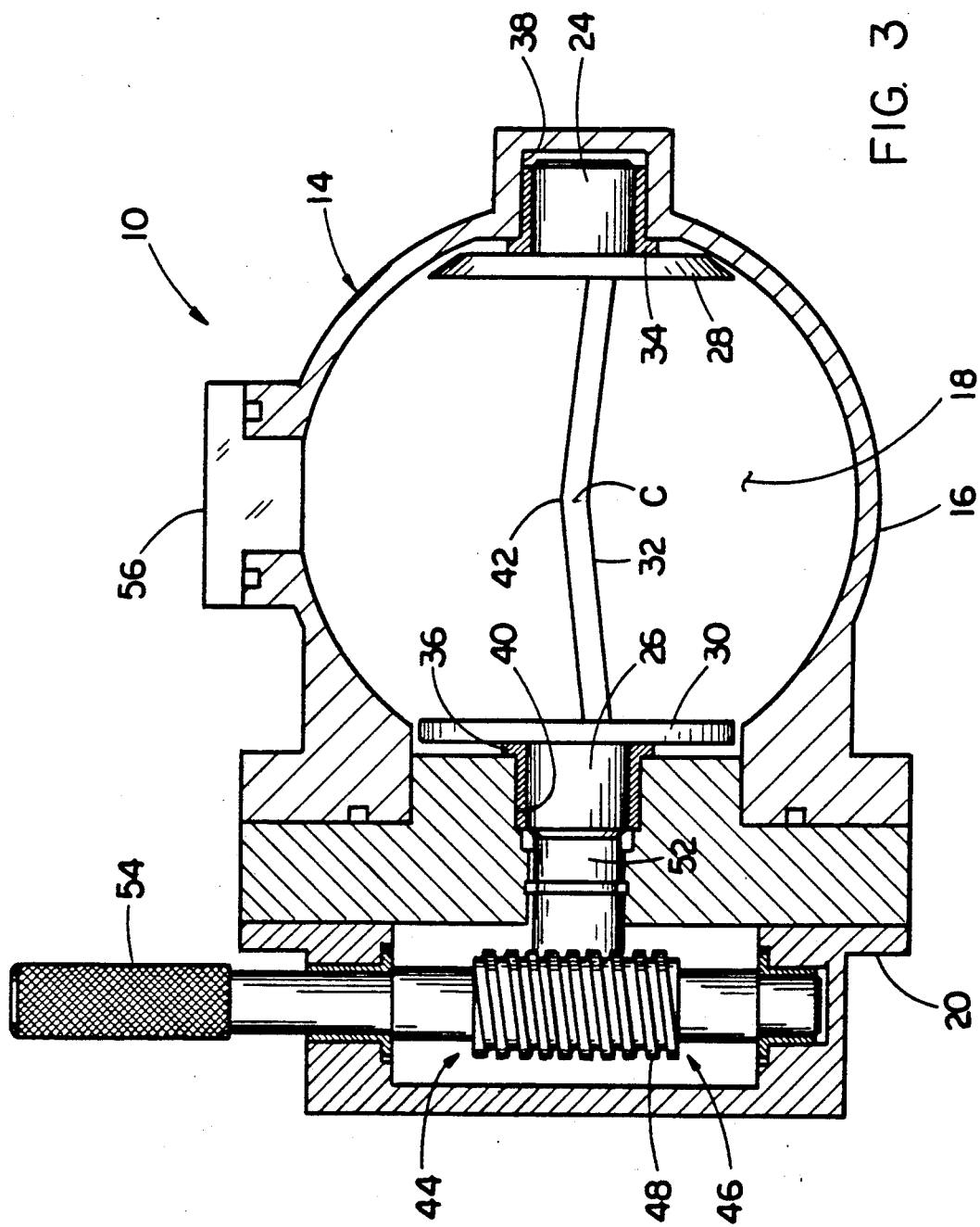
FIG. 3 is a transverse sectional view of the instrument taken along line 3—3 of FIG. 1.

In the following description, like reference characters designate like or corresponding parts throughout the several views. Also in the following description, it is to be understood that such terms as "forward", "rearward", "left", "right", "upwardly", "downwardly", and the like, are words of convenience and are not to be construed as limiting terms.

Referring now to the drawings, and particularly to FIGS. 1-4, there is shown a measuring instrument of the present invention, generally designated 10, which can directly and accurately measure on-line the effective partial pressure of dissolved gases in a liquid. The measuring instrument 10 is particularly useful in calculating the cavitation performance (such as required NPSHr) of a centrifugal pump 12 (FIG. 9) for which the actual vapor pressure of the pumped liquid is required. However, the measuring instrument 10 has application anywhere the total effective partial pressure of dissolved gases in a liquid media is desired to be known accurately and quickly. The effective partial pressure of any dissolved gases in a liquid can be accurately determined on-line with the measuring instrument 10 described herein without requiring any knowledge of the types of gases in the liquid solution.

Referring to FIGS. 1-4, the on-line measuring instrument 10 includes a housing 14 having a cylindrical tubular portion 16 defining a hollow flow chamber 18 and a casing portion 20 attached to the tubular portion 16. The flow chamber 18 is open at its opposite ends 18A and can be connected in flow communication with a conduit (not shown) which carries a flowing stream of liquid to be investigated.

Referring also to FIGS. 5-8, the instrument 10 further includes an elongated streamlined member 22 which is composed of outer and inner cylindrical spindles 24, 26, outer and inner circular end plates 28, 30 being disposed in spaced parallel planes and attached to the respective spindles 24, 26, and a shallow V-shaped wing 32 attached at its opposite ends to the outer and inner end plates 28, 30 and extending transversely across the flow chamber 18. The outer and inner spindles 24, 26 are rotatably mounted by respective outer and inner bearings 34, 36 disposed within respective outer hub recess 38 and inner cylindrical bore 40 of the housing 14.

The V-shaped wing 32 is attached to and extends between the outer and inner end plates 28, 30 in a substantially offset relation relative to an axis A of the streamlined member 22 defined by the common axes of the outer and inner spindles 24, 26. An apex 42 of the V-shaped wing 32 intersects with the axis A of the streamlined member 22 and also with an axis or center C of the tubular portion 16 of the housing 14 defining the flow chamber 18 and thus with the center of the stream of liquid flowing through the chamber 18.

The offset relation of the wing 32 relative to the rotational axis A of the member 22 ensures that only a point P on the apex 42 of the V-shaped wing 32 lies both on the transverse rotational axis A and the housing tubular portion center C. The point P will remain located at the center C of the stream of liquid no matter how the angle of attack of the wing 32 is changed relative to the stream of liquid flowing through the chamber 18. The angle of attack of the V-shaped wing 32 of the member 22 can be changed relative to the stream of liquid flowing through the housing chamber 18 by rotation of the member 22 at its spindles 24, 26 relative to the bearings 36, 38.

Referring to FIGS. 1-4, the instrument 10 also includes an adjusting mechanism 44 rotatably mounted to the casing portion 20 of the housing 14 and coupled to streamlined member 22. The adjusting mechanism 44 is actuatable for rotating the member 22 and thereby changing the angle of attack of the wing 32 relative to the stream of liquid flowing though the flow chamber 18 of the housing 14.

More particularly, the adjusting mechanism 44 includes a drive train 46 in the form of an arrangement of a worm shaft 48 and a worm gear 50 rotatably mounted to casing portion 20 of the housing 14. The worm gear 48 is journalled on a stub shaft 52 rigidly attached to and projecting from the inner spindle 26 of the member 22. The adjusting mechanism 44 also includes a knob 54 for manually gripping and rotating the worm shaft 52. The worm shaft and gear arrangement is self-locking so as to prevent the fluid forces against the wing 32 from causing it to rotate. The arrangement also has very little backlash to minimize flutter of the wing.

The instrument 10 also incorporates a suitable means for identifying the onset or occurrence of incipient cavitation bubbles at the point P of the wing 32 as the member 22 is rotated to change the angle of attack of the wing. In the embodiment illustrated in full in FIGS. 1-3, the bubble identifying means is a transparent viewing window 56 mounted in the tubular portion 16 of the housing 14. Alternatively, the bubble identifying means is a collimated light source 58 and a light detector 60, such as a photocell, both shown in dashed line schematical form in FIG. 2 which can identify the bubbles by detecting the scattering of light beam by the occurrence of the bubbles. Another alternative form of the bubble identifying means is a detector 62, such as a hydrophone, also shown in dashed line schematical form in FIG. 2 which can identify the bubbles by detecting the energy emitted upon collapse of the bubbles. The latter alternative is useful in the investigation of opaque liquids such as liquid metals.

The theory of operation of the instrument 10 is as follows. When a flowing liquid is forced to change direction by the presence of an obstruction, there is a deviation in the flow streamlines and a local decrease in static pressure. When the static pressure drops below the effective vapor pressure of the liquid, dissolved gas will come out of solution and/or the fluid will vaporize; when the local pressure increases above the effective vapor pressure of the liquid, the gas will go back into solution and/or the vapor bubbles will collapse. Because in a long, straight run of pipe the velocity of the fluid is highest at the center of the pipe, then the static pressure is lowest at the center and a perturbation to the flow stream equal over the entire cross-sectional area of the flowing liquid will cause bubble formation/cavitation first at the center of the flow stream. The V-shaped wing 32 of the instrument 10 ensures that lead edge cavitation/bubble formation occurs first in only one area (the apex 42 of the V in the vicinity of point P) so that all monitoring instruments can concentrate in the local area.

Figure 9:
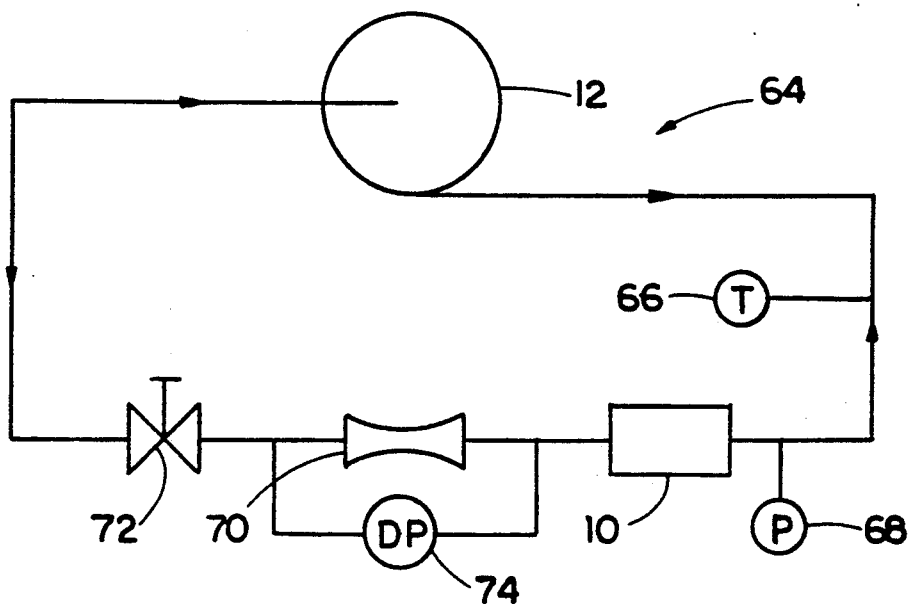
FIG. 9 is a diagrammatic view of a test setup incorporating the on-line measuring instrument of the invention.
Figure 10:
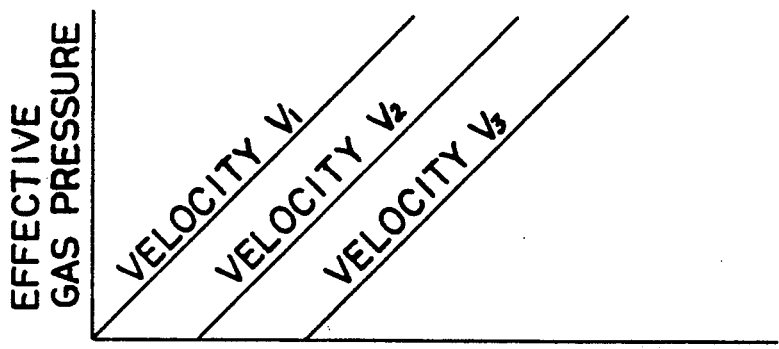
FIGS. 10 and 11 are examples of calibration graphs of the functional relationships between effective gas pressure and gas bubble formation angle of attack developed for a given liquid.
Figure 11:
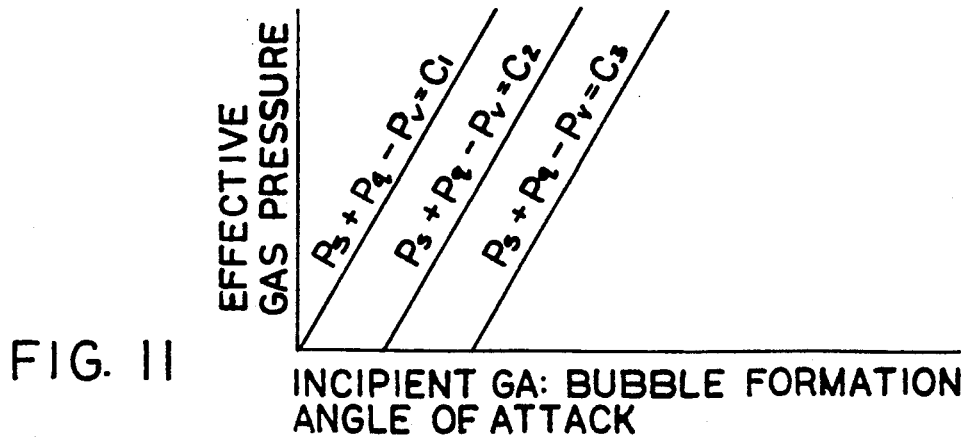

FIG. 9 is a diagram of a test setup 64 incorporating the on-line measuring instrument 10 of the invention. The setup 64 also includes a temperature indicator 66, a pressure indicator 68, a flow meter 70, and a flow control valve 72, all being connected in series with the instrument 10 and a pump 12 being measured A differential pressure indicator 74 is connected in parallel with the flow meter 70. In the alternative, not shown, the instrument 10 may be installed in a secondary flow loop with its own pressure indicator 68, flow meter 70, flow control valve 72, and differential pressure indicator 74 in lieu of the primary loop (as shown), depending on flow requirements. For given liquid conditions of static pressure, temperature, average fluid velocity and gas content, initiation of vapor/bubble formation at the apex 42 of the V-shaped wing 32 is a function of the angle of attack. For example, holding static pressure, temperature, and average fluid velocity constant, the angle-of-attack necessary to initiate bubble formation will decrease with increasing gas content of the liquid. If the gas content angle-of-attack function is known (through calibration of the instrument) the determination of the angle-of-attack necessary to initiate bubble formation allows immediate calculation of the gas content and holding the angle-of-attack constant while changing static pressure allows immediate calculation of the effective gas pressure. Examples of the types of functional relationships for a given liquid that can be developed through calibration are as illustrated in FIGS. 10 and 11.

Note that a feedback mechanism can be used with either the collimated light source 58 or the hydrophone 62 to adjust the angle-of-attack such that incipient bubble formation is either always occurring or the angle-of-attack is zero. Feeding all information to a microprocessor or equivalent will allow continual updating of gas content and effective gas pressure, as required It is thought that the present invention and many of its attendant advantages will be understood from the foregoing description and it will be apparent that various changes may be made in the form, construction and arrangement of the parts of the invention described herein without departing from the spirit and scope of the invention or sacrificing all of its material advantages, the forms hereinbefore described being merely preferred or exemplary embodiments thereof.

I claim:

1. An instrument for measuring on-line the effective partial pressure of dissolved gases in a liquid, said instrument comprising:
   (a) a housing having a flow chamber for connecting in flow communication with a flowing stream of liquid to be measured;
   (b) an elongated member rotatably mounted to said housing and extending across said flow chamber for presenting different angles of attack to the stream of liquid flowing through said housing chamber, said member having a point which remains located at a center of the stream of liquid flowing through said housing chamber as the angle-of-attack of said member is changed relative to the stream of liquid;
   (c) means coupled to said member for rotating and thereby changing the angle of attack of said member relative to the stream of liquid; and
   (d) means coupled to said housing for identifying the occurrence of incipient cavitation bubbles at said point of said member.

2. The instrument as recited in claim 1, wherein said member includes a V-shaped wing rotatably mounted at its opposite ends to said housing.

3. The instrument as recited in claim 2, wherein said point of said member is on an apex of said wing.

4. The instrument as recited in claim 1, wherein said member includes a pair of axially-spaced cylindrical spindles rotatably mounted to said housing.

5. The instrument as recited in claim 4, wherein said member includes:
   a pair of end plates attached to said respective spindles; and
   a shallow V-shaped wing attached at its opposite ends to said end plates and extending transversely across said housing flow chamber.

6. The instrument as recited in claim 4, wherein said wing is attached to and extends between said end plates in an offset relation relative to a rotational axis of said member.

7. The instrument as recited in claim 6, wherein said wing has an apex which intersects with said axis of said member and also with a center of said flow chamber through said housing and thus with a center of a stream of liquid flowing through said chamber such that only a point on said wing apex lies both on said rotational axis and at the center of the stream of liquid and will thereby remain located at the center of the stream of liquid no matter how the angle of attack of said wing is changed relative to the stream of liquid flowing through said chamber.

8. The instrument as recited in claim 1, wherein said means for rotating said member includes a drive train rotatably mounted to said housing and drivingly coupled to said member.

9. The instrument as recited in claim 8, wherein said drive train is a worm shaft and gear arrangement.

10. The instrument as recited in claim 9, wherein said means for rotating said member also includes a knob connected on said worm shaft for manually gripping and being rotatably mounted to said housing.

11. The instrument as recited in claim 1, wherein said means for identifying the bubbles is a transparent viewing window mounted in said housing.

12. The instrument as recited in claim 1, wherein said means for identifying the bubbles is a light source and detector arrangement for identifying the bubbles by detecting the scattering of light beam by the occurrence of the bubbles.

13. The instrument as recited in claim 1, wherein said means for identifying the bubbles is a detector for identifying the bubbles by detecting acoustic energy emitted upon collapse of the bubbles.

14. An instrument for measuring on-line the effective partial pressure of dissolved gases in a liquid, said instrument comprising:
  (a) a housing having a flow chamber for connecting in flow communication with a flowing stream of liquid to be measured;
  (b) an elongated member rotatably mounted to said housing, said member including a V-shaped wing having an apex and extending across said flow chamber for presenting different angles of attack to the stream of liquid flowing through said housing chamber, said wing of said member having a point on said apex thereof which remains located at a center of the stream of liquid flowing through said housing chamber as the angle-of-attack of said wing is changed relative to the stream of liquid;
  (c) an adjustable mechanism coupled to said member for rotating and thereby changing the angle of attack of said wing of said member relative to the stream of liquid; and
  (d) a viewing window mounted in said housing for identifying the occurrence of incipient cavitation bubbles at said point of said wing.

15. The instrument as recited in claim 14, wherein said member includes a pair of axially-spaced cylindrical spindles rotatably mounted to said housing.

16. The instrument as recited in claim 15, wherein said member includes a pair of end plates attached to said respective spindles, said wing being attached at opposite ends to said end plates and extending transversely across said housing flow chamber.

17. The instrument as recited in claim 16, wherein said wing is attached to and extends between said end plates in an offset relation to a rotational axis of said spindles.

18. The instrument as recited in claim 14, wherein said wing is disposed in offset relation to a rotational axis of said member.

19. The instrument as recited in claim 18, wherein said wing has an apex which intersects with said axis of said member and also with a center of said flow chamber through said housing and thus with a center of a stream of liquid flowing through said chamber such that only a point on said wing apex lies both on said rotational axis and at the center of the stream of liquid and will thereby remain located at the center of the stream of liquid no matter how the angle of attack of said wing is changed relative to the stream of liquid flowing through said chamber.

20. The instrument as recited in claim 14, wherein said means for rotating said member includes a drive train rotatably mounted to said housing and drivingly coupled to said member.

21. The instrument as recited in claim 20, wherein said drive train is a worm shaft and gear arrangement.

22. The instrument as recited in claim 20, wherein said means for rotating said member also includes a knob connected on said worm shaft for manually gripping and being rotatably mounted to said housing.

* * * * *